United States Patent
Sunkel et al.

(10) Patent No.: US 6,806,291 B1
(45) Date of Patent: Oct. 19, 2004

(54) ANALGESIC COMPOUNDS, THEIR SYNTHESIS AND PHARMACEUTICAL COMPOSITIONS CONTAINING THEM

(75) Inventors: Carlos Sunkel, Madrid (ES); Julio Alvarez-Builla, Madrid (ES); Nicolas G. Bazan, New Orleans, LA (US); Anthony Vaccarino, Destrahan, LA (US)

(73) Assignee: The Foundation for the LSU Health Sciences Center, New Orleans, LA (US)

( * ) Notice: Subject to any disclaimer, the term of this patent is extended or adjusted under 35 U.S.C. 154(b) by 0 days.

(21) Appl. No.: 10/682,744

(22) Filed: Oct. 9, 2003

(51) Int. Cl.$^7$ ...................... A61K 31/195; C07C 311/18
(52) U.S. Cl. ............... 514/562; 514/214.03; 514/227.2; 514/279; 514/282; 514/289; 514/330; 514/396; 562/430
(58) Field of Search ................... 514/214.03, 227.2, 514/279, 282, 289, 330, 396, 562; 562/430

(56) References Cited

U.S. PATENT DOCUMENTS

| | | | | |
|---|---|---|---|---|
| 3,700,773 A | * | 10/1972 | Shen et al. | 514/166 |
| 5,324,749 A | * | 6/1994 | Woog et al. | 514/562 |
| 5,554,636 A | | 9/1996 | Bazan et al. | |
| 5,621,110 A | | 4/1997 | Bazan et al. | |
| 6,417,229 B1 | * | 7/2002 | Sahagan et al. | 514/530 |

* cited by examiner

*Primary Examiner*—Peter O'Sullivan
(74) *Attorney, Agent, or Firm*—Adams and Reese LLP

(57) ABSTRACT

New analgesic compounds, which are prepared by the hydrolysis of N-acylated 4-hydroxyphenylamine derivatives, their synthesis and pharmaceutical compositions containing them are disclosed. These compounds surprisingly possess high analgesic activity with little hepatotoxic effect, making them more useful than conventional non-steroidal anti-inflammatory drugs (NSAIDs) in the treatment of chronic pain.

17 Claims, 2 Drawing Sheets

ANALGESIC COMPOUNDS, THEIR SYNTHESIS AND PHARMACEUTICAL COMPOSITIONS CONTAINING THEM

FIELD OF THE INVENTION

The present invention relates to new analgesic compounds prepared by the hydrolysis of N-acylated 4-hydroxyphenylamine derivatives, the synthesis of these compounds and pharmaceutical compositions containing them. These compounds surprisingly possess high analgesic activity with little hepatotoxic effect, making them more useful than conventional non-steroidal anti-inflammatory drugs (NSAIDs) in the treatment of chronic pain.

BACKGROUND OF THE INVENTION

Analgesics, such as acetaminophen and other NSAIDs, have been used for some time for the treatment of pain. However, the morbidity associated with the hepatotoxic activity means that due care must be exercised when administering these drugs. There are approximately 100,000 cases of acetaminophen overdose annually, with approximately 30 deaths resulting. (Clissold, 1980; McGoldrick et al. 1997). Acetaminophen has a toxic metabolite, N-acetyl-benzoquinoneimine (NAPQI), which depletes hepatic and renal glutathione, a cytoprotective endogenous metabolite (Mason & Fischer, 1986; Mitchell et al., 1983). Hepatic and renal toxicity with acetaminophen can occur at doses only 4- to 8-fold higher than the maximum recommended analgesic dose (Neuberger et al., 1980). Pharmaceutical combinations that contain acetaminophen and a centrally acting analgesic may be even more dangerous than acetaminophen alone. With repeated use these combinations require higher doses to produce the same analgesic effect because of an increase in tolerance. As the dose of the combination is increased to compensate for analgesic tolerance, the safety of the drug decreases as the higher doses of the acetaminophen component increase hepatic and renal toxicity.

In U.S. Pat. No. 5,554,636 (Bazan et al.) and U.S. Pat. No. 5,621,110 (Bazan et al.), two of the inventors herein disclosed the series of N-acylated 4-hydroxyphenylamine derivatives linked via an alkylene bridge to the nitrogen atom of a 1,2-benzisothiazol-3(2H)-one 1,1-dioxide group, referred to as the SCP series, along with the process for their preparation and methods of their use for alleviating pain. The disclosures of these patents are incorporated herein by reference. The SCP series is structurally depicted by the following general formula I:

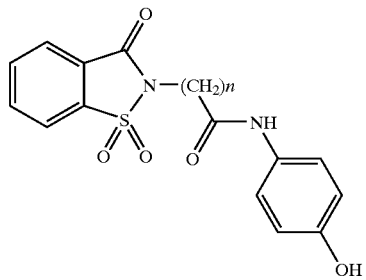

wherein n is a number from 1 to 5. These new non-narcotic analgesics surprisingly possess high analgesic activity, do not suppress blood coagulation, and display little hepatotoxic effect.

In addition, in U.S. patent application Ser. No. 10/292,105 (Bazan et al.), the disclosure of which is also incorporated by reference, two of the inventor's herein also disclosed pharmaceutical combinations, comprising an opioid or a non-opioid analgesic in an intimate admixture with an analgesic from the SCP series, which surprisingly exhibited synergistic analgesia.

In continued search for new, more selective molecules with greater pharmacological potency, it has been ascertained that N-acylated-4-hydroxyphenylamine derivatives, linked via an alkylene bridge to the nitrogen atom of a 2-sulfamoyl benzoic acid group surprisingly possess high analgesic activity and little hepatotoxic effect.

SUMMARY OF THE INVENTION

The present invention relates to new analgesic compounds prepared by the hydrolysis of N-acylated 4-hydroxyphenylamine derivatives. The new analgesic compounds have the general formula II:

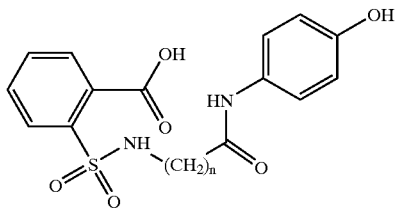

in which n is a number between 1 and 5.

Some specific examples of the present invention, without, however, limiting it, are the following:

2-{[(4-hydroxyphenyl)carbamoyl]methylsulfamoyl}benzoic acid;
2-{[(4-hydroxyphenyl)carbamoyl]ethylsulfamoyl}benzoic acid;
2-{[(4-hydroxyphenyl)carbamoyl]proylsulfamoyl}benzoic acid;
2-{[(4-hydroxyphenyl)carbamoyl]butylsulfamoyl}benzoic acid;
2-{[(4-hydroxyphenyl)carbamoyl]pentylsulfamoyl}benzoic acid;

The compounds of general formula II, which are referred to generally as the SCP-M series, may be prepared by the hydrolysis of compounds in the SCP series with 1N aq. NaOH at room temperature, and the product can be purified by recrystallization in ethanol.

The present invention also includes the formation of pharmaceutically acceptable, stable salts of SCP-M series compounds with metals or amines. Examples of metals used in cations are alkali metals such as Na or K and alkaline-earth metals such as Mg and Ca. Examples of amines include N,N-dibenzylethylendiamine, chloroprocaine, choline, diethanolamine, ethylendiamine, N-methylglucamine and procaine.

In addition, the present invention includes pharmaceutical compositions comprising a compound from the SCP-M series in combination with opioid and non-opioid analgesics.

Figure 1:
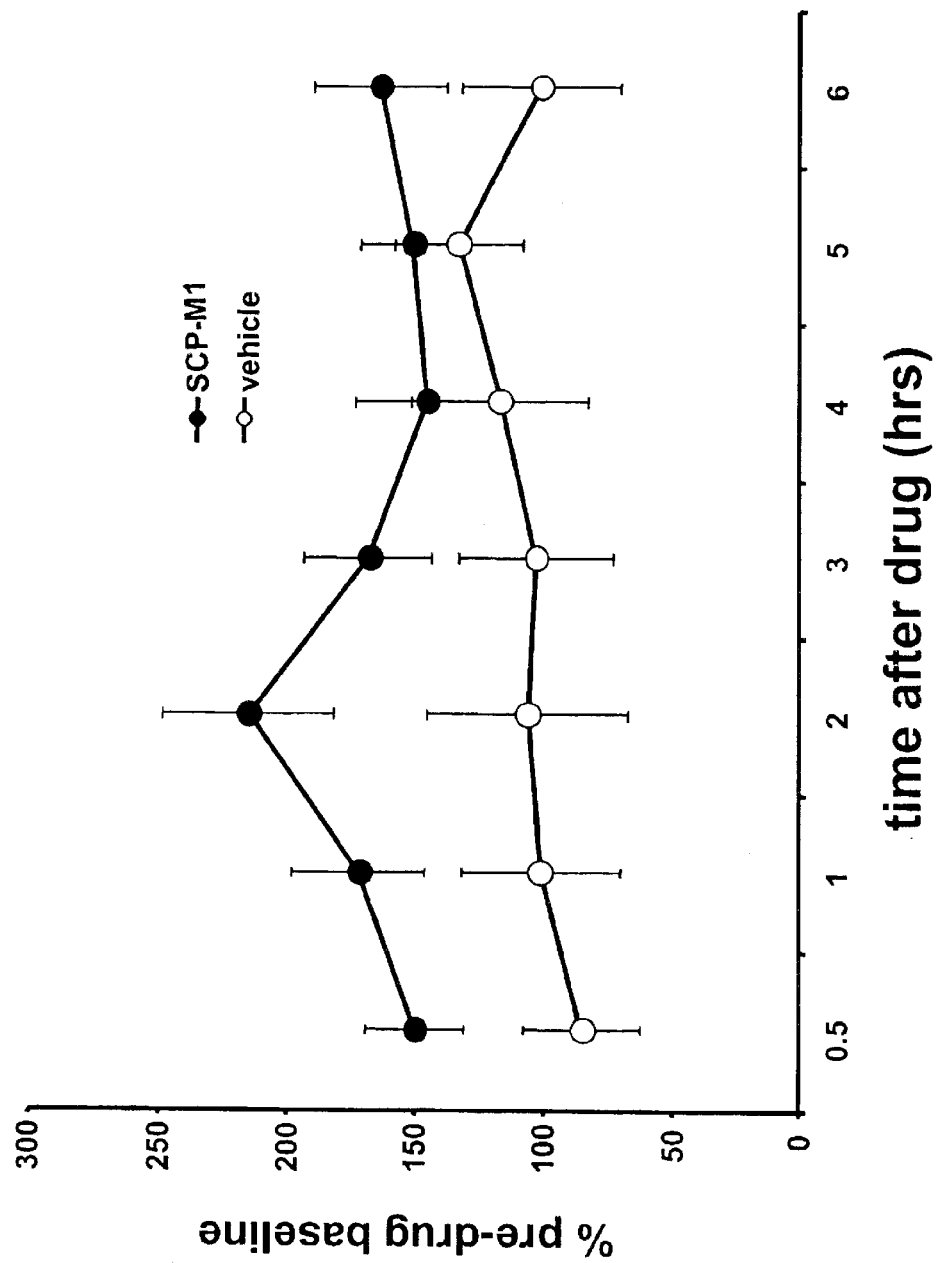
FIG. 1 is the effect of SCP-M1 on CFA-induced thermal hyperalgesia shown as a percentage of pre-drug baseline.

The compounds of the present invention may be administered alone or mixed with a pharmaceutical vehicle selected in accordance with the administration route and standard pharmaceutical practice, e.g. orally, rectally, topically, parenterally, and intrathecally. They may be administered orally, either in the form of tablets containing excipients such as starch or lactose, or in capsules, either alone or mixed with excipients, or in the form of syrups or suspensions containing coloring or flavoring agents. They may also be injected parenterally, for example intramuscularly, intravenously or subcutaneously. In parenteral administration, they can preferably be used in the form of a sterile aqueous solution, which can contain other solutes, such as, for example, any salt or glucose in order to make the solution isotonic.

Intrathecal administration can be delivered by either spinal tap injection or by catheterization. Intrathecal drug administration can avoid the inactivation of some drugs when taken orally as well and the systemic effects of oral or intravenous administration. Additionally, intrathecal administration permits use of an effective dose that is only a fraction of the effective dose required by oral or parenteral administration. Furthermore, the intrathecal space is generally wide enough to accommodate a small catheter, thereby enabling chronic drug delivery systems.

Intrathecal treatment of chronic pain is primarily performed by use of an intrathecal pump. The pump may be surgically placed under the skin of the patient's abdomen. One end of a catheter is connected to the pump, and the other end of the catheter is threaded into a CSF filled subarachnoid or intrathecal space in the patient's spinal cord. The implanted pump can be programmed for continuous or intermittent infusion of the drug through the intrathecally located catheter.

The compounds of the present invention may be administered for the treatment of pain, for example orally, either covered in gelatin capsules or compressed in lozenges. For oral therapeutic administration, said compounds may be mixed with excipients and used in the form of lozenges, tablets, capsules, elixirs, suspensions, syrups, wafers, chewing gum, and the like. These preparations could contain at least 0.5% and up to about 99% of active compound, but can vary depending on each form. Preferably, oral preparations will contain between 2% and 50% approximately of the weight of each unit. The amount of active compound in such compositions should be that which is necessary for obtaining the corresponding dosage. The compositions and preparations obtained according to the present invention are prepared in such a way that each oral dosage unit can contain between about 0.1 and about 1000 mg of the active compound.

In parenteral therapeutic administration, the active compounds of this invention should be incorporated in a solution or suspension. These preparations could contain at least 0.1% of the active compound, but preferably varies between 0.5% and 50% approximately of the weight of the preparation. The amount of active compound in such compositions should be that which is necessary for obtaining the corresponding dosage. The compositions and preparations obtained according to the present invention are prepared in such a way that each parenteral dosage unit can contain between 0.5 and 1000 mg of the active compound. While intramuscular administration may be given in a single dose or divided into up to three doses, intravenous administration can include a drip device for giving the dose by venoclysis. Parenteral administration of the preparation may be performed by means of ampoules, disposable syringes or multiple-dose vials made of glass or plastic.

In intrathecal therapeutic administration, the active compounds of this invention may be employed with or without diluents or may be reconstituted with autologous spinal fluid. Intrathecal administrations could contain at least 0.1 $\mu$g of the active compound, but can contain between 0.1 and 100 $\mu$g of the active compound.

Of necessity, there will be variations that will depend on the weight and conditions of the subject to be treated and on the particular administration route selected.

As stated above, the present invention also includes pharmaceutical compositions comprising a compound from the SCP-M series in combination with opioid and non-opioid analgesics. The drugs that comprise the group known as the opioid analgesics include among others the phenanthrene alkaloids of opium, comprising morphine, codeine, and thebaine. While thebaine produces no analgesia, it is an important intermediate in the production of semisynthetic opioids. Other agents with structures and function related to morphine include: (1) the morphine analogs, such as hydromorphone, oxymorphone, hydrocodone, and oxycodone; (2) Diels-Alder adducts, such as etorphine and buprenorphine; (3) the morphinan derivatives, such as dextromethorphan and butorphanol; (4) the benzomorphan derivatives, such as phenazocine, pentazocine and cyclazocine; (5) the piperidine derivatives, such as meperidine and anileridine; and (6) open chain analgesics (methadone type compounds), such as methadone and propoxyphene. The drugs that comprise the group known as the non-opioid analgesics include: (1) N-methyl-D-aspartate (NMDA) receptor antagonists, such as dextromethorphan and ketamine and other antagonists that suppress central sensitization by competing for any of the binding site subcategories associated with the NMDA receptor, e.g., the glycine binding site, the phenylcyclidine (PCP) binding site, etc., as well as the NMDA channel; (2) alpha$_2$ adrenoreceptor agonists, such as clonidine, metomidine, detomidine, dexmetomidine, dexmedetomidine and xylazine, that reduce the release of norepinephrine; (3) other agents, such as tramadol, often mistakenly referred to as an opioid, that produce analgesia by their inhibitory actions on monoamine re-uptake rather than by agonist effect; (4) non-steroidal anti-inflammatory drugs such as aspirin, ibuprofen and other drugs that inhibit cyclooxygenase enzymes and (5) mixed agonist-antagonist analgesics such as buprenorphine, dezocine, nalbuphine.

The pharmaceutical combinations of the present invention comprise an opioid or a non-opiod analgesic in an intimate admixture with an analgesic from the SCP-M series along with a pharmaceutically acceptable carrier prepared according to conventional pharmaceutical techniques. Pharmaceutically acceptable carriers include solid or liquid fillers, diluents, and encapsulating substances. The amount of the carrier employed in conjunction with the combination is sufficient to provide a practical quantity of material per unit dose of analgesic.

Pharmaceutically acceptable carriers for oral administration include, sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration include isotonic saline, propylene glycol, ethyl oleate, pyrrolidone, aqueous ethanol, sesame oil, corn oil, and combinations thereof.

Various oral dosages forms can be employed, including solid forms such as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, and reconstituted solutions and/or suspensions.

Pharmaceutically effective combinations can contain between 0.1 and 1000 mg of an analgesic from the SCP-M series. The preferred pharmaceutically effective combinations contain between 400 and 1000 mg of an analgesic from the SCP-M series. The pharmaceutically effective amounts of the opioid and non-opioid analgesics in combination with analgesics in the SCP-M series are similar to the corresponding combinations of opioid and non-opioid analgesics with acetaminophen.

Biological Results

To determine whether the SCP-M series has analgesic activity, its effect on Complete Freund's Adjuvant (CFA)—induced thermal hyperalgesia was accessed. Under halothane anesthesia, male CD-1 mice were injected with 0.1 ml of CFA (Calbiochem, USA) to the glabrous surface of one hind paw. When injected into the footpad, CFA produces localized inflammation and hyperalgesia that appears within two hours and is present for 7 to 10 days (Iadorola, et al., 1988). At 48-hours post-CFA (time of peak hyperalgesia), each mouse received by oral gavage 2.5 mmol/kg of SCP-M1 or vehicle. The latency to withdraw the paw from a thermal stimulus (Hargreaves, et al., 1988) was measured using an analgesiometer (IITC Life Sciences, Inc., Woodland Hills, Calif.) according to the technique of Hargreaves, et al. The stimulus intensity was set to produce baseline latencies of about 10–15 seconds, and a 20 second maximum latency was used. Thermal hyperalgesia was measured before drug administration (pre-drug baseline), and again at 30 minutes, 1 hour, 2 hour, 3 hour, 4 hour, 5 hour, and 6 hour after drug administration.

Analysis of variance between groups (ANOVA; drug×time) revealed a significant drug effect (F1, 15=7.740, p=0.014), indicating a significant analgesic effect of SCP-M1 as compared with vehicle treated controls. No other statistically significant effects were found (time effect: F(6, 90)=0.486, p=0.817; drug×time interaction: F(6,90)=0.634, p=0.793). The effects of SCP-M1 on CFA-induced thermal hyperalgesia are shown as a percentage of pre-drug baseline in FIG. 1.

Figure 2:
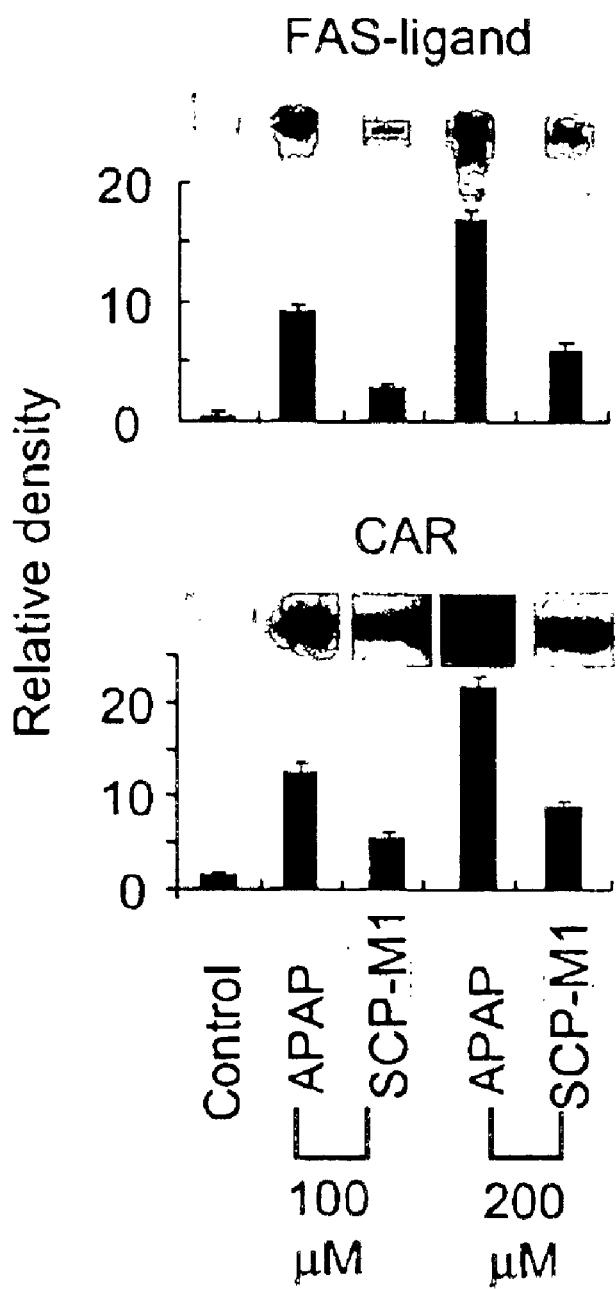
FIG. 2 is a comparison of the effects of SCP-M1 and acetaminophen on pro-apoptotic FAS-ligand up-regulation and CAR activation.

In addition to high analgesic activity, the SCP-M series displays little or no hepatotoxic effect. The hepatotoxic effects of SCP-M1 were evaluated in human hepatocytes (HEPG-2) and in human primary cultures of normal liver cells. Acetaminophen, a known hepatotoxic analgesic, was used as a positive control. Phase contrast, microscopy, Trypan blue exclusion, Hoechst staining, and FAS-ligand and CAR (constitutive androstane receptor) induction were used as criteria. In human hepatocytes (HEPG-2), Hoechst staining indicated that SCP-M1 was practically ineffective in inducing cell death, whereas acetaminophen induced severe apoptotic cell death. In human hepatocytes in primary cultures, analysis of the hepatotoxic effects of SCP-M1 and acetaminophen measured by the Trypan blue exclusion and Hoechst staining showed that the hepatotoxic effects exerted by these compounds were very much comparable to those in HEPG-2 cells, enhanced apoptosis was caused by acetaminophen but not SCP-M1. As can be seen in FIG. 2, pro-apoptotic FAS-ligand up-regulation and CAR activation were significantly enhanced by acetaminophen in human primary liver cultures, whereas SCP-M1 produced reduced effects.

HEPG-2 cells were grown and maintained in EMEM medium containing NEAA (nonessential amino acids), supplemented with 10% fetal bovine serum (FBS), and incubated at 37° C. with a constant supply of 5% $CO_2$. Primary human liver cells were grown in HCM medium (Walkersville, Md.), and maintained in HMM medium (Walkersville, Md.) at 37° C. with 5% $CO_2$. 80% confluent cultures of HEPG2 and primary hepatocytes growing in 6- and 24-well plates, respectively were held 6–8 hr in serum-free medium (EMEM, 0.5% FBS for HEPG2 and HMM [Clonetics, Walkersville, Md.] for primary hepatocytes) before the addition of analgesics. The serum-starved cells were treated with SCP-M1 or acetaminophen for 6–8 hr at 37° C.

Hoechst staining was employed for detection of apoptosis. Spent medium was removed from the experimentally treated cells, which were washed with 2 ml PBS (room temperature). Hoechst solution (2 ml, 2 μM final concentration) was added to the cells, and they were incubated at 37° C. 45 min. Apoptotic cell death was detected by confocal microscope under fluorescent illumination.

The up-regulation of FAS-ligand (FAS-L) and activation of CAR (constitutive androstane receptor) were analyzed by Western blot. Briefly, the cell extracts were made, and adjusted for protein concentrations by the Bio-rad method. About 15–20 µg protein were loaded onto an 8–16% gel (Bio-rad), and electrophoresis was conducted for 2 hr at 120 V. The proteins were transferred onto nitrocellulose membrane at 30 V for 60 min at 4° C. The membranes were probed with either FAS-L- or CAR (human)-specific antibodies (Santa Cruz Biotechnology, Santa Cruz, Calif.) and phosphorylation of the FAS-L and CAR was detected by ECL kit. Quantitation of phosphorylation of FAS-L and CAR proteins was by densitometry. The results are shown in FIG. 2.

Synthesis

The SCP-M series compounds may be prepared according to the following reaction scheme:

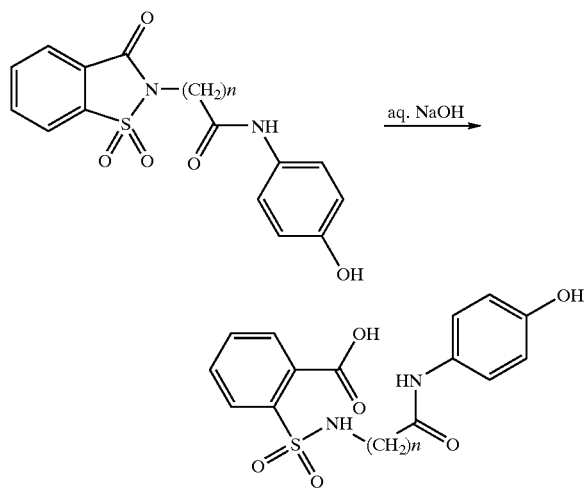

EXAMPLES

The following non-limiting example illustrates the present invention.

A solution of 2-(2,3-dihyrdo-3-oxo-1,2-benzisothiazol-2-yl-1,1-dioxide)-N-(4-hydroxyphenyl)acetamide (0.5 g. 1.5 mmol) in 3 ml of 1N aq. NaOH was stirred for 20 minutes at room temperature. The solution was then acidified with 1N aq. HCL, and was extracted with AcOEt. The organic phase was washed with brine, dried over magnesium sulphate, filtered, and concentrated, to give an oil, which was titrated with hexane-$Cl_2CH_2$ (1:1). The product, SCP-M1 was finally obtained by recrystallization in ethanol as a white residue (420 mg) with a melting point of 193–195° C. (Yield: 80%).

| Analysis for: $C_{15}H_{14}N_2O_6S$ | % C | % H | % N |
|---|---|---|---|
| Calculated | 51.42 | 4.03 | 8.00 |
| Found | 51.70 | 3.86 | 8.27 |

It is apparent from the instant specification that various modifications and changes may be made by those skilled in the art. It is therefore intended that the following claims be interpreted as covering all modifications and changes that fall within the true spirit and scope of the invention.

What is claimed is:

1. A substantially pure compound of the formula II,

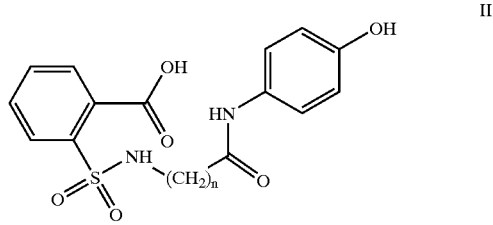

wherein n is a number from 1 to 5.

2. A pharmaceutical composition that displays analgesic activity with limited hepatotoxic effect, containing at least one compound of formula II as claimed in claim 1.

3. A method for the treatment of pain, which comprises the administration of an effective dose of a compound as claimed in claim 1 to a subject affected by pain.

4. A process for preparing a compound of formula II,

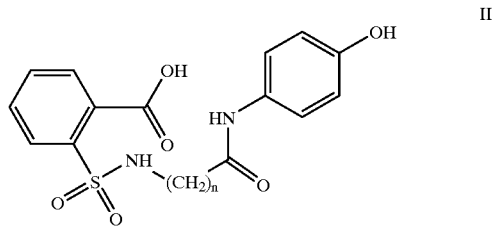

comprising:
reacting a compound of formula I, wherein n is a number from 1 to 5,

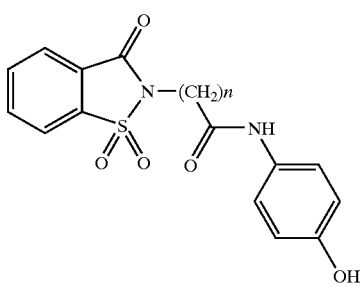

with aqueous sodium hydroxide, to give a compound of formula II.

5. An analgesic composition comprising, safe, and pharmaceutically effective amounts of:

(a) an opioid analgesic;
(b) a non-narcotic analgesic of the general formula,

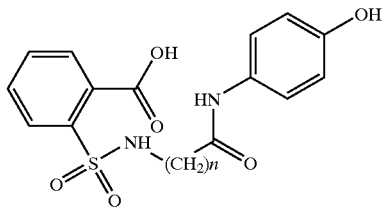

wherein n is a number from 1 to 5; and
(c) a pharmaceutically acceptable carrier.

6. A composition according to claim 5, wherein the opioid analgesic is a phenanthrene alkaloid of opium.

7. A composition according to claim 5, wherein the opioid analgesic is a morphine analog.

8. A composition according to claim 5, wherein the opioid analgesic is a synthetic derivative of thebaine.

9. A composition according to claim 5, wherein the opioid analgesic is a morphinan derivative.

10. A composition according to claim 5, wherein the opioid analgesic is a benzomorphan derivative.

11. A composition according to claim 5, wherein the opioid analgesic is a piperidine derivative.

12. A composition according to claim 5, wherein the opioid analgesic is an open chain opioid analgesic.

13. An analgesic composition comprising synergistic, safe, and pharmaceutically effective amounts of:

(a) a non-opioid analgesic;
(b) a non-narcotic analgesic of the general formula,

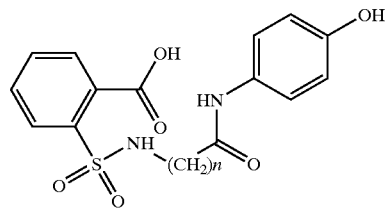

wherein n is a number from 1 to 5; and
(c) a pharmaceutically acceptable carrier.

14. A composition according to claim 13, wherein the non-opioid analgesic is an NMDA receptor antagonist.

15. A composition according to claim 13, wherein the non-opioid analgesic is an $alpha_2$ adrenoreceptor agonist.

16. A composition according to claim 13, wherein the non-opioid analgesic is a monoamine re-uptake inhibitor.

17. A composition according to claim 13, wherein the non-opioid analgesic is a mixed agonist-antagonist analgesic.

* * * * *